United States Patent
Fan et al.

(10) Patent No.: US 10,214,721 B2
(45) Date of Patent: *Feb. 26, 2019

(54) METHOD FOR MAKING CULTURE MEDIUM

(71) Applicants: Tsinghua University, Beijing (CN); HON HAI PRECISION INDUSTRY CO., LTD., New Taipei (TW)

(72) Inventors: Li Fan, Beijing (CN); Chen Feng, Beijing (CN); Wen-Mei Zhao, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 109 days.

This patent is subject to a terminal disclaimer.

(21) Appl. No.: 15/216,716

(22) Filed: Jul. 22, 2016

(65) Prior Publication Data
US 2016/0326486 A1    Nov. 10, 2016

Related U.S. Application Data

(63) Continuation of application No. 13/563,980, filed on Aug. 1, 2012, now Pat. No. 9,433,703.

(30) Foreign Application Priority Data

Aug. 1, 2011  (CN) .......................... 2011 1 0217845

(51) Int. Cl.
| | | |
|---|---|---|
| C12N 5/00 | (2006.01) | |
| A61L 27/38 | (2006.01) | |
| A61L 27/56 | (2006.01) | |
| C12M 1/12 | (2006.01) | |
| C12M 1/22 | (2006.01) | |
| A61L 27/08 | (2006.01) | |
| B05D 1/02 | (2006.01) | |
| B05D 3/00 | (2006.01) | |

(52) U.S. Cl.
CPC ............ *C12N 5/0068* (2013.01); *A61L 27/08* (2013.01); *A61L 27/383* (2013.01); *A61L 27/3878* (2013.01); *A61L 27/56* (2013.01); *B05D 1/02* (2013.01); *B05D 3/007* (2013.01); *C12M 23/10* (2013.01); *C12M 25/10* (2013.01); *A61L 2400/12* (2013.01); *A61L 2430/32* (2013.01); *C12N 2533/10* (2013.01)

(58) Field of Classification Search
CPC .............. C12N 5/0068; C12N 2533/10; A61L 2400/12; A61L 2430/32; A61L 27/08; C12M 23/10; B05D 1/02; B05D 3/007
See application file for complete search history.

(56) References Cited

U.S. PATENT DOCUMENTS

| | | | | |
|---|---|---|---|---|
| 5,866,249 | A  * | 2/1999 | Yarusso et al. | ............... 428/355 |
| 8,796,024 | B2 * | 8/2014 | Fan et al. | ...................... 435/402 |
| 8,828,725 | B2 * | 9/2014 | Fan et al. | ...................... 435/404 |
| 9,433,703 | B2 * | 9/2016 | Fan et al. | ............. A61L 27/383 |
| 2008/0238294 | A1* | 10/2008 | Xu et al. | ....................... 313/498 |
| 2009/0160796 | A1* | 6/2009 | Jiang et al. | ................... 345/173 |
| 2009/0267000 | A1* | 10/2009 | Chen et al. | ................ 250/492.1 |

OTHER PUBLICATIONS

Galvan-Garcia et al., "Robust cell migration and neuronal growth on pristine carbon nanotube sheets and yarns", J. Biomater. Sci. Polymer Edn., 2007, vol. 18, No. 10, pp. 1245-1261. (Year: 2007).*
Wang K., "Neural Stimulation with a Carbon Nanotube Microelectrode Array", Nano Letters, 2006, vol. 6, No. 9, pp. 2043-2048. (Year: 2006).*

* cited by examiner

*Primary Examiner* — Satyendra K Singh
(74) *Attorney, Agent, or Firm* — ScienBiziP, P.C.

(57) ABSTRACT

A method for making a culture medium for culturing neural cells is provided. An original carbon nanotube structure is provided. The original carbon nanotube structure includes a drawn carbon nanotube film including a number of carbon nanotubes joined end to end by van der Waals force. The carbon nanotubes are substantially oriented along the same direction. A carbon nanotube structure including a number of carbon nanotube wires spaced from each other is formed by treating the original carbon nanotube structure. The carbon nanotube structure is fixed on a substrate.

15 Claims, 12 Drawing Sheets

METHOD FOR MAKING CULTURE MEDIUM

RELATED APPLICATIONS

This application is a continuation application of U.S. patent application Ser. No. 13/563,980, filed on Aug. 1, 2012, entitled "NEURAL GRAFT," which claims all benefits accruing under 35 U.S.C. § 119 from China Patent Application No. 201110217845.2, filed on Aug. 1, 2011 in the China Intellectual Property Office, the disclosure of which is incorporated herein by reference.

BACKGROUND

1. Technical Field

The present disclosure relates to a neural graft.

2. Discussion of Related Art

Many people suffer from neurological disorders as a result of neuron injuries. Neural grafting can provide relief from these injuries. Neural grafting is a surgical transfer of tissue from various sources into specific areas of the nervous system that have been affected by injury. The neural grafting serves as a "bridge" to connect the proximate injured neurons. Grafted cells may synthesize and release growth-promoting factors near the injured neurons, thereby promoting neuron regeneration.

What is needed, therefore, is to provide a neural graft employed in the wound, for prompt healing.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
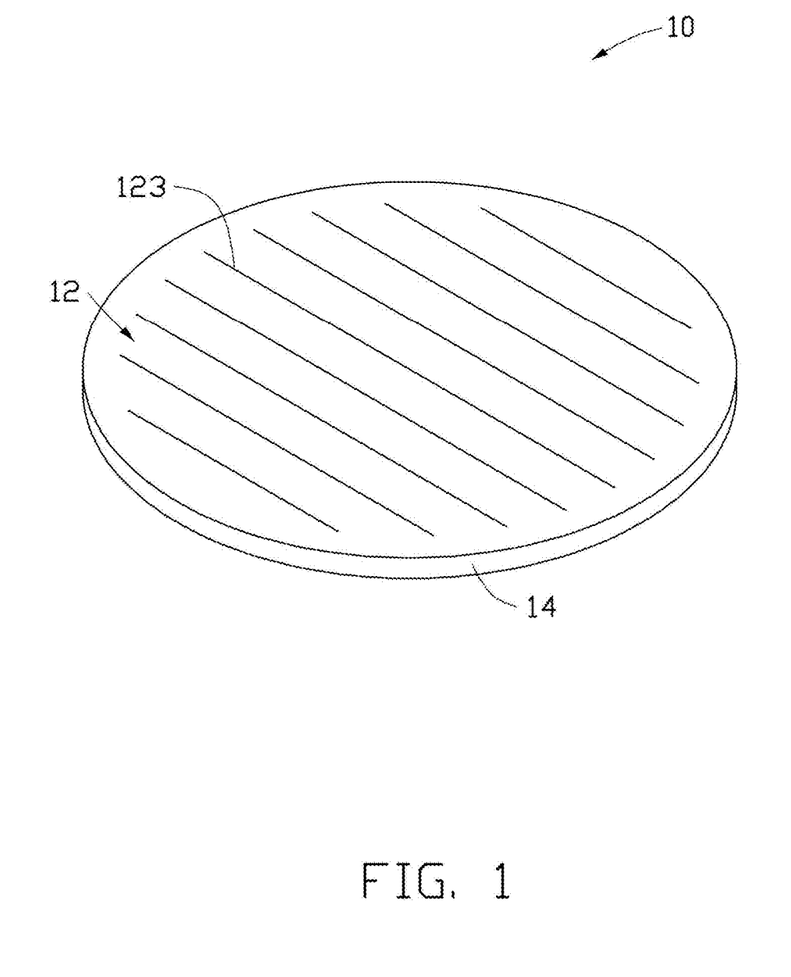
FIG. 1 is an isometric view of one embodiment of a culture medium.

FIG. 1, illustrates one embodiment of a culture medium 10 used to culture neural cells. Each neural cell includes a neural cell body and at least one neurite branched from the neural cell body. The culture medium 10 includes a carbon nanotube structure 12 and a substrate 14. The carbon nanotube structure 12 is located on and makes contact with the substrate 14 by van der Waals force.

The carbon nanotube structure 12 includes a plurality of carbon nanotubes orderly arranged. The term 'orderly' describes the carbon nanotubes being arranged in a consistently systematic manner, e.g., the carbon nanotubes are arranged approximately along a same direction and or have two or more sections within each of which the carbon nanotubes are arranged approximately along a same direction (different sections can have different directions). In one embodiment, the carbon nanotube structure 12 consists of a plurality of carbon nanotubes orderly arranged. The carbon nanotube structure 12 can be a "free-standing" structure having carbon nanotubes joined with each other by van der Waals force. That is, the carbon nanotube structure 12 can retain a specific shape without any support because of the van der Waals force between adjacent carbon nanotubes. In addition, the carbon nanotube structure 12 connected by van der Waals attractive force can bend easily without breaking. Thus, the carbon nanotube structure 12 can have good elasticity and ductility, thereby allowing the carbon nanotube structure 12 to be tailored and employed to cure a wound having any shape.

The carbon nanotube structure 12 can be patterned by including a number of carbon nanotube wires 123 spaced from or crossed with each other. A diameter of each carbon nanotube wire 123 can range from about 1 micrometer to about 10 micrometers. A distance between two adjacent carbon nanotube wires 123 can be equal to or larger than a diameter of the neural cell body. In one embodiment, the distance between two adjacent carbon nanotube wires 123 ranges from about 20 micrometers to about 100 micrometers. If the carbon nanotube wires 123 in the carbon nanotube structure 12 are crossed, the carbon nanotube wires 123 can define a number of pores. An effective diameter of each pore is equal to or larger than the diameter of the neural cell body. In one embodiment, the effective diameter of each pore ranges from about 20 micrometers to about 100 micrometers.

In one embodiment, the distance between two adjacent carbon nanotube wires 123 or the effective diameter of each pore is equal to or larger than the diameter of the neural cell body. The neurons are grown on the culture medium 10, and the neuron cells will be absorbed on the surface of the substrate 14. The carbon nanotube wires 123 can guide growing directions of the neurites. The neurites can grow along the carbon nanotube wires 123. Thus, the arrangement of the carbon nanotube wires, the distance between adjacent carbon nanotube wires, or the effective diameter of pores in the carbon nanotube structure 12 can be arranged to form a patterned carbon nanotube structure 12. The patterned carbon nanotube structure 12 can control the growing directions of the neurites such that the neurons can be grown oriented in any desired direction.

The carbon nanotube wire 123 includes a number of carbon nanotubes orderly arranged. The carbon nanotube wire 123 can include the carbon nanotubes joined end to end by van der Waals force. The carbon nanotubes in the carbon nanotube wire 123 can be substantially oriented along a same direction or spirally arranged along the axial direction of the carbon nanotube wire 123.

Figure 2:
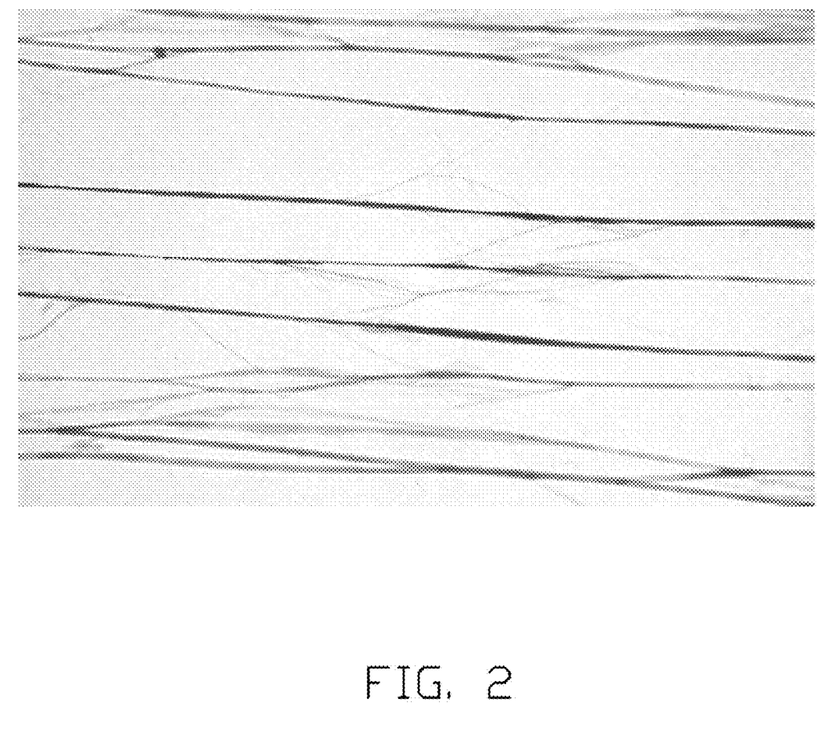
FIG. 2 is a transmission electron microscope (TEM) image of one embodiment of a carbon nanotube film.

The carbon nanotube structure 12 can be a free standing film. The carbon nanotube structure 12 can include at least one carbon nanotube film. Referring to FIG. 2, the carbon nanotube film can include a number of carbon nanotube wires juxtaposed and separated from each other. At least one carbon nanotube in the carbon nanotube film is located between adjacent carbon nanotube wires and combines with the adjacent carbon nanotube wires by van der Waals force. The carbon nanotube wires in the carbon nanotube film are substantially arranged along a single direction. The carbon nanotube film can be a free standing structure by combining adjacent carbon nanotube wires with the at least one carbon nanotube. In one embodiment, a number of carbon nanotubes are joined with two adjacent carbon nanotube wires by van der Waals force. In one embodiment, each carbon nanotube wire consists of carbon nanotubes joined end to end along the axial direction of the carbon nanotube wire.

Figure 3:
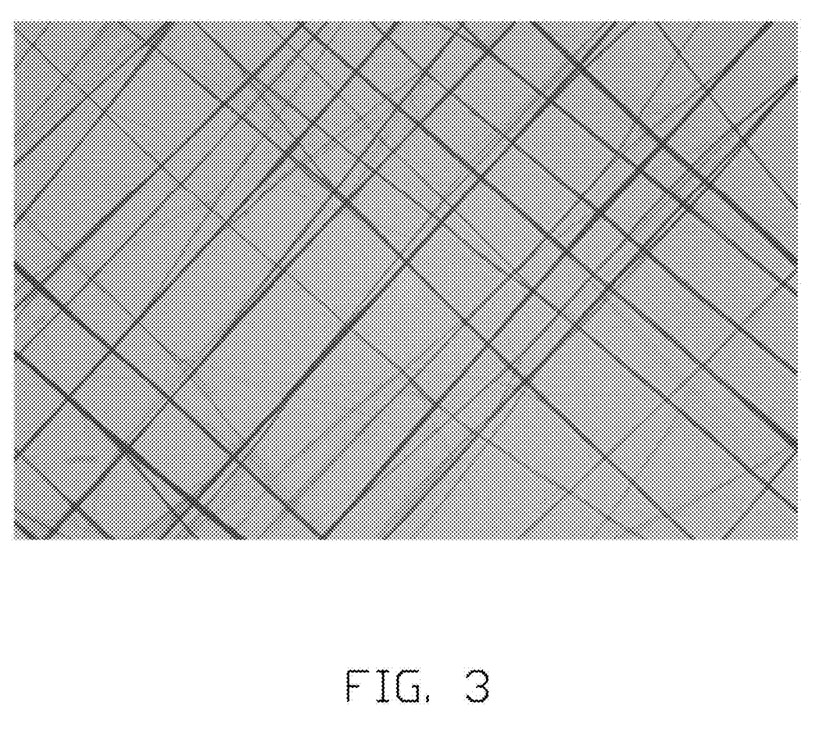
FIG. 3 is a TEM image of one embodiment of stacked carbon nanotube films.

In one embodiment, the carbon nanotube structure 12 includes a number of stacked carbon nanotube films shown in FIG. 3. Adjacent carbon nanotube films in the carbon nanotube structure 12 are combined by van der Waals force, and the carbon nanotube wires in two adjacent carbon nanotube films defines angles along the axial direction of the carbon nanotube wires. The angles can be larger than or equal to 0 degrees, and less than or equal to 90 degrees.

A surface of the carbon nanotube structure 12 can be polarized to a polar surface, during a process of culturing neuronal cells using the culture medium 10. The carbon nanotubes in the surface of the carbon nanotube structure 12 are polarized. Charges on the surface of the carbon nanotube structure 12 are changed after the surface of the carbon nanotube structure 12 is formed into the polar surface. Surface charge polarities of the carbon nanotubes in the polar surface of the carbon nanotube structure 12 are opposite to surface charge polarities of the neural cells. As such, the surface charge polarities of the carbon nanotubes in the polar surface and the surface charge polarities of the neural cells attract each other. The surface charge polarities of the carbon nanotubes in the polar surface and the surface charge polarities of the neural cells can have attractive forces between them. Therefore, the surface charge of the polar surface is different from that of the neural cells, and the neural cells can be absorbed on the polar surface.

The carbon nanotube structure 12 is electrically conductive, thermally conductive, and acoustical, due to the excellent electrical conductivity, thermal conductivity, and acoustic property of the carbon nanotubes. The neuronal cells can be grown by stimulation from electricity, heat, or phonation. Therefore, the neuronal cells are grown orderly on the culture medium 10, which is beneficial for researching the effect of electricity, heat, or phonation on the neuronal cells.

The substrate 14 can be used to lay or support the carbon nanotube structure 12 and the pre-cultured neuronal cells. The shape, material, and thickness of the substrate 14 can be selected as desired. In one embodiment, the shape of the substrate 14 is substantially the same as that of the carbon nanotube structure 12, and the carbon nanotube structure 12 completely covers a surface of the substrate 14. The substrate 14 can be a planar structure or a curved structure, such as quadrate sheet-shaped structure, arc-shaped structure, stepped structure.

The material of the substrate 14 can be a biocompatible material. The biocompatible material can be a biodegradable material, non-biotoxic material, or carbon nanotube sheet-shaped material. For example, the biodegradable material can be thermoplastic starch, polylactide, polyvinyl alcohol, or aliphatic polyesters. The non-biotoxic material can be silicone. The carbon nanotube sheet-shaped material consists of carbon nanotubes. The carbon nanotube sheet-shaped material has a free-standing property and a certain mechanical strength, such as a carbon nanotube film or a carbon nanotube net structure. The substrate 14 can be flexible, such as silicone or a carbon nanotube material. As such, the culture medium 10 can be also flexible.

In other embodiments, the material of the substrate 14 can be a non-biocompatible material. The non-biocompatible material can be plastic, such as polystyrene. The substrate 14 can be a plastic culture vessel, a plastic watch glass, or a plastic sheet-shaped structure. If the substrate is a plastic culture vessel or a plastic watch glass, the culture medium 10 can be stored directly as culture cells without the need of another container to load the culture medium 10 and the cells.

In one embodiment, the substrate is made of a biocompatible material. The culture medium 10 can be transplanted into a biological body and form a shape as desired. The shape and the thickness of the culture medium 10 can be designed as a shape and thickness of a wound on the biological body. If the culture medium 10 is transplanted into the wound, the neuronal cells close to the wound can regenerate to re-communicate with and re-connect to each other, thus the wound can be rehabilitated. If the thickness of the carbon nanotube structure 12 is thin, the mechanical strength of the carbon nanotube structure 12 will be small, and the surface area of the carbon nanotube will be large. The carbon nanotube structure 12 can be easily broken by an outer force and easily adhere to other objects. Thus, the carbon nanotube structure 12 will not be easily broken and can avoid adhering to hydrophilic objects because the carbon nanotube structure 12 is located on the substrate 14. The carbon nanotube structure 12 fixed on the substrate 14 can be easy to transfer.

Figure 4:
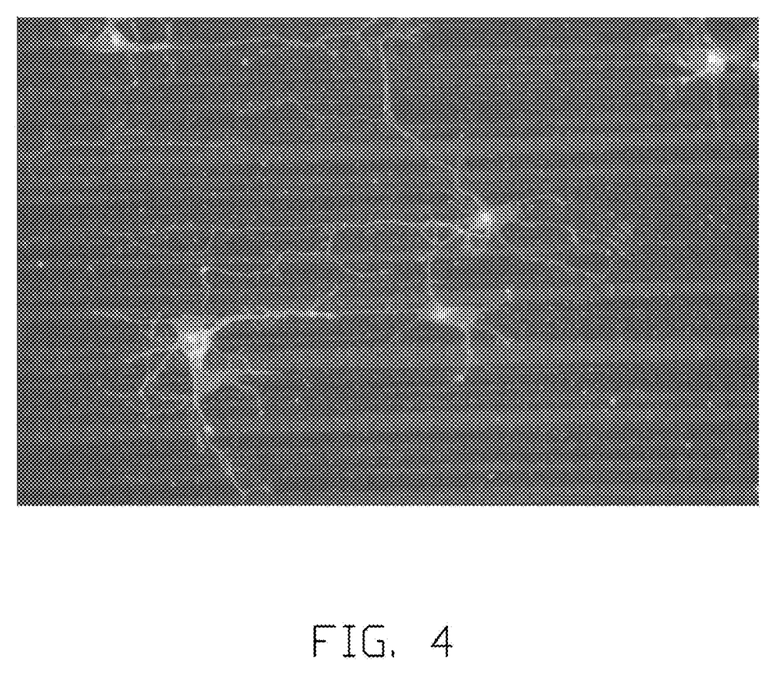
FIG. 4 is an optical microscopy image of one embodiment of neurons stained with fluorescence, wherein the neurons are cultured by using the culture medium shown in FIG. 1.

In one embodiment, the culture medium 10 consists of a circular and sheet-shaped plastic substrate and a carbon nanotube structure consisting of a single carbon nanotube film. The carbon nanotube film includes a number of carbon nanotube wires 123 extending substantially along a same direction and separated from each other. The carbon nanotube wires 123 are substantially parallel to each other. At least one carbon nanotube is combined with and connects the two adjacent carbon nanotube wires 123. The distance between the two adjacent carbon nanotube wires is larger than or equal to 30 micrometers, and less than or equal to 60 micrometers. Each carbon nanotube wire 123 includes a number of carbon nanotubes substantially oriented along the extending direction of the carbon nanotube wire 123. Thus, if the neuronal cells are cultured on the culture medium 10, the neuronal cells are absorbed on the surface of the circular and sheet-shaped plastic substrate. Neurites differentiated from the neuronal cells shown in FIG. 4 are substantially linearly grown along the axial direction of the carbon nanotube wires 123.

Figure 5:
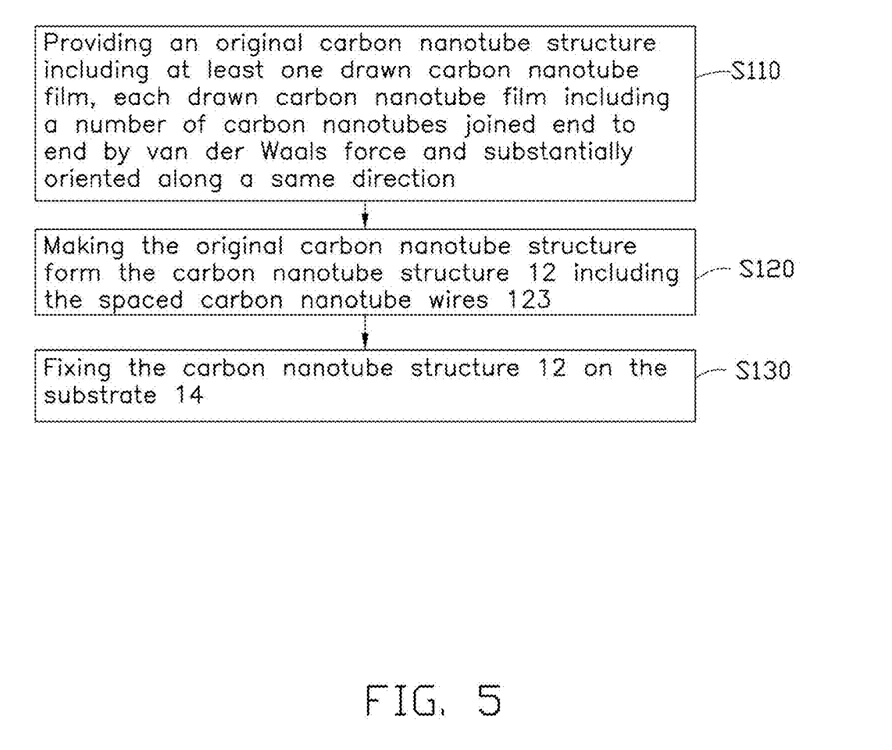
FIG. 5 is a flow chart of one embodiment of a method for making a culture medium.

Referring to FIG. 5, if the carbon nanotube wires in the carbon nanotube structure 12 are spaced from each other, one embodiment of a method for making the culture medium 10 includes:

S110, providing an original carbon nanotube structure including at least one drawn carbon nanotube film including a number of carbon nanotubes joined end to end by van der Waals force and substantially oriented along a same direction;

S120, forming the carbon nanotube structure 12 including the spaced carbon nanotube wires 123 from the original carbon nanotube structure; and S130, fixing the carbon nanotube structure 12 on the substrate 14.

Figure 6:
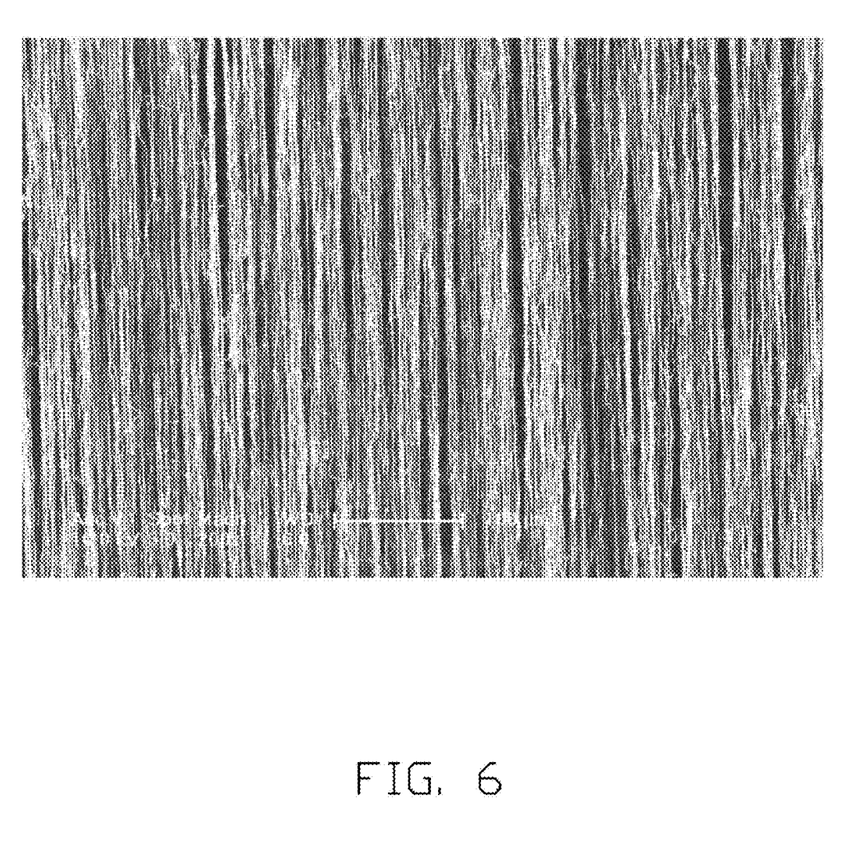
FIG. 6 is a scanning electron microscope (SEM) image of one embodiment of a drawn carbon nanotube film.

In step S110, the drawn carbon nanotube film is a free-standing structure consisting of carbon nanotubes. Referring to FIG. 6, the drawn carbon nanotube film includes a plurality of carbon nanotubes that can be arranged substantially parallel to a surface of the drawn carbon nanotube film. A large number of the carbon nanotubes in the drawn carbon nanotube film can be oriented along a preferred orientation, meaning that a large number of the carbon nanotubes in the drawn carbon nanotube film are arranged substantially along a single direction. In the drawn carbon nanotube film, an end of one carbon nanotube is joined to another end of an adjacent carbon nanotube arranged substantially along the same direction by van der Waals attractive force. A small number of the carbon nanotubes are randomly arranged in the drawn carbon nanotube film, and has a small if not negligible effect on the larger number of the carbon nanotubes in the drawn carbon nanotube film arranged substantially along the same direction. The carbon nanotubes oriented substantially along the same direction may not be perfectly aligned in a straight line, and some curve portions may exist. Some carbon nanotubes located substantially side by side in contact with each other cannot be excluded.

Figure 7:
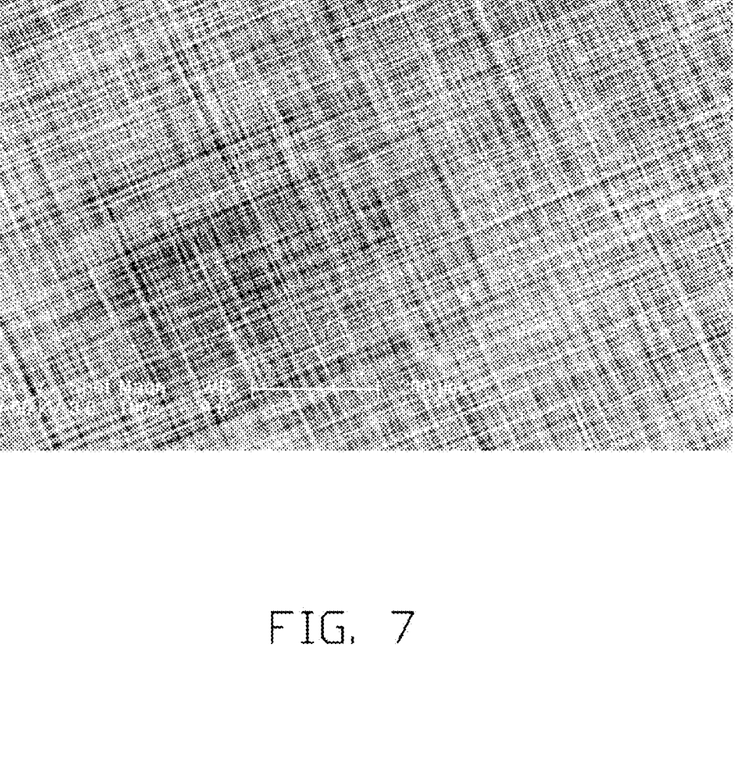
FIG. 7 is an SEM image of one embodiment of stacked carbon nanotube films.

In one embodiment, the original carbon nanotube structure includes a number of stacked drawn carbon nanotube films as shown in FIG. 7. Adjacent drawn carbon nanotube films can be adhered by only the van der Waals attractive force therebetween. An angle can exist between the carbon nanotubes in adjacent drawn carbon nanotube films. The angle between the aligned directions of the adjacent drawn carbon nanotube films can be in a range from about 0 degrees to about 90 degrees. In one embodiment, the angle between the aligned directions of the adjacent drawn carbon nanotube films is about 90 degrees. Simultaneously, aligned directions of adjacent drawn carbon nanotube films can be substantially perpendicular to each other, thus a plurality of micropores and nodes can be defined by the original carbon nanotube structure.

The drawn carbon nanotube film can be made by the following steps: providing a carbon nanotube array; and drawing the carbon nanotube film from the carbon nanotube array.

The step S120 can include the following steps:

S121, suspending the original carbon nanotube structure; and

S122, treating the suspended original carbon nanotube structure using a solvent to form the carbon nanotube structure 12 including a number of carbon nanotube wires 123.

In step S121, the original carbon nanotube structure can be suspended by fixing two opposite sides of the original carbon nanotube structure. In one embodiment, most of the carbon nanotubes extend substantially along a single direction, the two opposite sides of the original carbon nanotube structure are substantially perpendicular to the extending direction of the carbon nanotubes, and the two opposite sides of the original carbon nanotube structure are fixed. In one embodiment, the original carbon nanotube structure is a single drawn carbon nanotube film drawn from a carbon nanotube array.

In step S122, after the original carbon nanotube structures are treated with solvent, juxtaposed carbon nanotubes in the original carbon nanotube structure will shrink, and the carbon nanotubes joined end-to-end substantially along a same direction will converge into parallel carbon nanotube wires. Thus, the carbon nanotube structure 12 is formed.

The step S122 can include the following steps: atomizing the solvent into a number of liquid drops, the diameters of the liquid drops being less than or equal to 10 micrometers; spraying the liquid drops into the surface of the original structure by a flowing gas to soak the original carbon nanotube structure; and evaporating the solvent in the original structure, so that under a surface tension of the soaked original carbon nanotube structure, the adjacent and parallel carbon nanotubes in the drawn carbon nanotube film converge and join end-to-end by van der Waals force to form a number of carbon nanotube wires juxtaposed and spaced from each other, thereby forming the carbon nanotube structure 12.

The solvent can be atomized by gas atomization, ultrasonic atomization, or adding aerosol. The solvent can be alcohol, methanol, acetone, acetic acid, water, or other volatile materials. In one embodiment, the solvent is alcohol. During the process of atomizing the solvent, the air pressure should be small, and the original carbon nanotube structure should not be broken. The carbon nanotube wires 123 in the carbon nanotube structure 12 are used to guide the neurites growing along the carbon nanotube wires 123. It is noted that there are a number of carbon nanotubes located between adjacent carbon nanotube wires 123 and combined with the adjacent carbon nanotube wires 123. The carbon nanotube structure 12 can be made by treating the original carbon nanotube structure, so the method for making the culture medium 10 is easy.

In one embodiment, the carbon nanotubes in the original carbon nanotube structure are substantially oriented along the same direction. Step S120 can be executed by applying a force substantially perpendicular to the axial direction of the carbon nanotubes in the original carbon nanotube structure. For example, the step S120 can further include the following steps:

providing at least one elastic supporter, such as a spring, elastic rubber, or rubber ring;

suspending the original carbon nanotube structure, the original carbon nanotube structure being at least partly fixing on the at least one elastic supporter; and drawing the at least one elastic supporter along an elastic drawing direction, to change distances between juxtaposed carbon nanotubes in the original carbon nanotube structure, wherein the elastic drawing direction is substantially perpendicular to the extending direction of the carbon nanotubes in the original carbon nanotube structure. Thus, the distances between juxtaposed carbon nanotubes can be increased or reduced.

In step S130, the carbon nanotube structure 12 is placed on a surface of the substrate 14. The carbon nanotube structure 12 is soaked by an organic solvent. The organic solvent in the carbon nanotube structure 12 is evaporated such that the carbon nanotube structure 12 is fixed on the surface of the substrate 14 by van der Waals force, because of the reduction of the surface tension of the carbon nanotube structure 12. The carbon nanotube structure 12 can be soaked by dropping or spraying the organic solvent on the surface of the substrate 14. The organic solvent can be the same as the solvent in step S122, such as alcohol, methanol, acetone, acetic acid, or other solvent which can be evaporated.

The method for making the culture medium 10 can also include: providing the carbon nanotube structure 12 including the carbon nanotube wires 123; and fixing the carbon nanotube structure 12 by treating the carbon nanotube structure 12 using the organic solvent. In one embodiment, the carbon nanotube wires 123 are untwisted carbon nanotube wires, which are directly drawn from a carbon nanotube array. In another embodiment, the carbon nanotube wires 123 are twisted carbon nanotube wires, which are made by twisting the untwisted carbon nanotube wires or a carbon nanotube film structure. The twisted carbon nanotube wire includes a plurality of carbon nanotubes substantially spiraling along an axial direction of the twisted carbon nanotube wire. The carbon nanotube structure 12 can be formed by locating the twisted or untwisted carbon nanotube wires side by side, or weaving the twisted or untwisted carbon nanotube wires.

Figure 8:
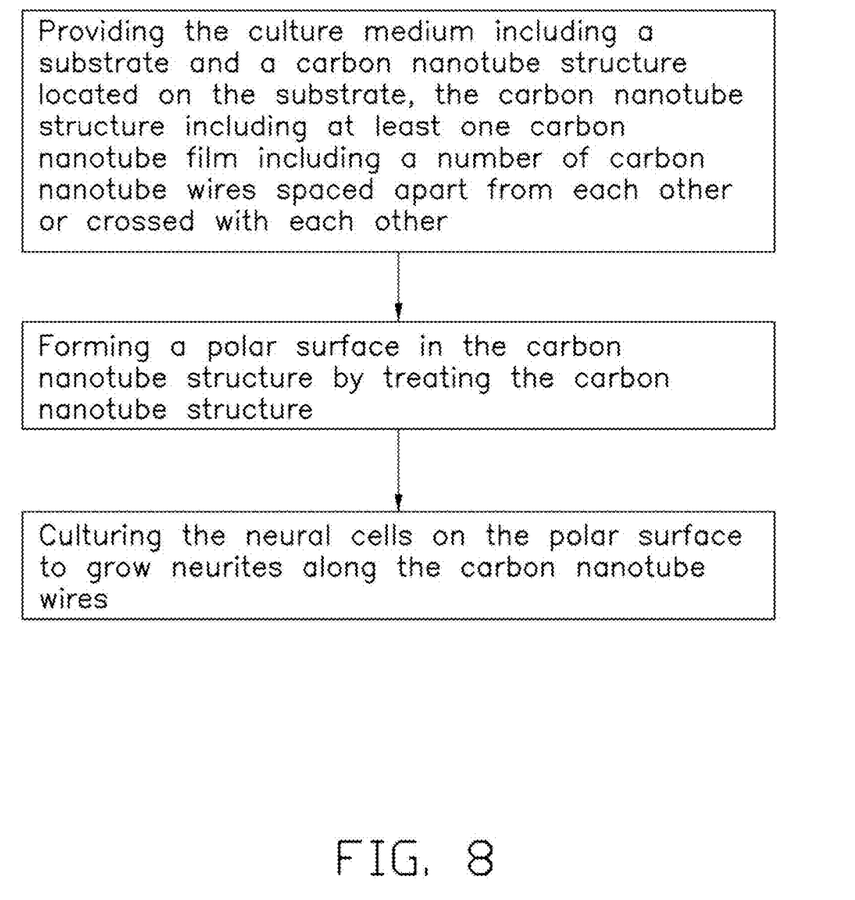
FIG. 8 is a flow chart of one embodiment of a method for growing neurons using the culture medium shown in FIG. 1.

Referring to FIG. 8, one embodiment of a method for culturing neural cells using the culture medium 10 can include:

Step A, providing the culture medium including a substrate and a carbon nanotube structure located on the substrate, the carbon nanotube structure including at least one carbon nanotube film including a number of carbon nanotube wires spaced apart from each other or crossed with each other;

Step B, forming a polar surface in the carbon nanotube structure by treating the carbon nanotube structure; and Step C, culturing the neural cells on the polar surface to grow neurites along the carbon nanotube wires.

One purpose of step B is to change the surface charge polarity of carbon nanotubes in a surface of the carbon nanotube structure. Thus, the polarized carbon nanotube structure can absorb and be biologically compatible with neural cells for neural cells adherent growth. "Compatible" in the text means the carbon nanotube structure and the neural cells can coexist. Step B can include the following steps:

B1, sterilizing the culture medium; and

B2, treating the carbon nanotube structure in the sterilized culture medium using a poly-D-lysine solution or polyetherimide solution.

In step B1, the culture medium can be sterilized by irradiating or heating, and the carbon nanotube structure is sterilized by ultraviolet light irradiating or heating. The method for sterilizing the culture medium is not limited, as long as the carbon nanotube structure is sterilized.

In step B2, the poly-D-lysine solution or polyetherimide solution is dropped onto the surface of the carbon nanotube structure, until the poly-D-lysine solution or polyetherimide solution covers the surface of the carbon nanotube structure. The surface of the carbon nanotube structure is covered with the poly-D-lysine solution or polyetherimide solution for more than 10 hours or until the surface of the carbon nanotube structure is polarized. The surface charge polarity of the polar surface of the carbon nanotube structure is different from the surface charge polarities of neural cells. The neural cells can be tightly absorbed on the polar surface. The polar surface of the carbon nanotube structure can provide a location for culturing the neural cells. The poly-D-lysine solution or polyetherimide solution covered on the carbon nanotube structure is rinsed using sterilized deionized water to reduce and prevent the poly-D-lysine solution or polyetherimide solution affecting the neural cells.

The carbon nanotube structure can be treated with the poly-D-lysine solution or polyetherimide solution to change the surface charge and form the polar surface. As such, it is unnecessary to treat the carbon nanotube structure with plating methods, coating methods, or chemical modifications, so that the carbon nanotube can absorb the neural cells. Therefore, the method for culturing neural cells is easy.

In one embodiment, the substrate in the culture medium is a sheet-shaped structure. The culture medium can be located in a container, such as a plastic culture vessel, or a plastic watch glass, to culture the neural cells. Thus, step B includes the sub-steps of: providing the container, and placing the culture medium in the container, the substrate contacting with the bottom surface of the container; sterilizing the container and the culture medium; and treating the culture medium with the poly-D-lysine solution or polyetherimide solution.

Step C can include sub-steps of:

C1, seeding a number of neuron cells on the polar surface of the carbon nanotube structure; and C2, growing the neuron cells seeded on the polar surface.

In step C1, a neuron solution is dropped onto the polar surface until the neuron solution completely covers the polar surface. The neuron solution is formed by dispersing a number of neuron cells into a planting solution. The neuron cells in the neuron solution are not differentiation cells, meaning the cells are in the original state or not mature, thus the neurites may not branch from the cells or the lengths of neurites are short. Therefore, the neuron cells seeded on the carbon nanotube structure are not branched neuron cells. The neurons can be mammalian neuron cells, such as hippocampal neuron cells.

In step C2, the neurons on the culture medium are incubated in an incubator with a $CO_2$ concentration of about 5% and a temperature of about 37□. During the optimal culture period, under guiding of the carbon nanotube wires in the carbon nanotube structure, a plurality of neurites from a cell body of the individual neuron cells will branch along the axial directions of the carbon nanotube wires and connect with adjacent neurons to form a neuronal network. Thus, the neurites can be grown in any desired direction or orientation. That is, the extending directions of the neurites can be controlled. The neuronal communication can be propagated.

When the culture medium is implanted into a wound of a human body or mammal body, neurites extending from a neuron cell will branch along the axial directions of the carbon nanotube wires until the neurites connect with ends or edges of the wound. Thus, the wound can be healed, and the neuronal communication can be regenerated.

Example

The method for culturing neural cells using the culture medium 10 includes the following steps.

A culture medium is provided. The culture medium consists of a circular sheet-shaped plastic substrate and a carbon nanotube structure located on the circular sheet-shaped plastic substrate. The carbon nanotube structure is formed by a single carbon nanotube film. The carbon nanotube structure includes carbon nanotube wires with diameters more than 1 micrometer, and less than or equal to 10 micrometers. The distance between adjacent carbon nanotube wires is greater than or equal to 30 micrometers, and less than or equal to 60 micrometers, especially the distance is about 50 micrometers.

The culture medium is fixed on the bottom of a plastic culture vessel. The circular sheet-shaped plastic substrate contacts the bottom of the plastic culture vessel. The plastic culture vessel with the culture medium fixed therein is put into an ultraviolet light sterilizing box. The culture medium and the plastic culture vessel are irradiated with ultraviolet light for about 2.5 hours to eliminate microorganisms, such as bacteria. The sterilized carbon nanotube structure is then treated with a poly-D-lysine solution having a concentration of about 20 μg/ml, until a surface of the carbon nanotube structure is completely covered by the poly-D-lysine solution. The carbon nanotube structure is soaked in the poly-D-lysine solution for about 20 hours. The poly-D-lysine solution on the surface of the carbon nanotube structure is removed by rinsing the carbon nanotube structure with sterilized deionized water. The surface of the carbon nanotube structure treated with poly-D-lysine solution is polarized and becomes a polar surface.

Under sterile conditions, a hippocampal neuron solution is dropped on the polar surface of the carbon nanotube structure until the hippocampal neuron solution substantially covers the polar surface. The hippocampal neuron cells in the hippocampal neuron solution are absorbed on the circular sheet-shaped plastic substrate.

The culture vessel with the hippocampal neuron cells on the culture medium is put in the incubator with a $CO_2$ concentration of about 5% and a temperature of about 37° C. for about 7 days. The hippocampal neuron cells are incubated in the incubator. During the optimal culture period, the feeding solution is replaced timely. Referring to FIG. 4, a number of neurites from a cell body of the individual hippocampal neuron cells are absorbed on the polar surface and branch along the carbon nanotube wires in the carbon nanotube structure. The neurites connect with adjacent hippocampal neuron cells to form a neuronal network.

Figure 9:
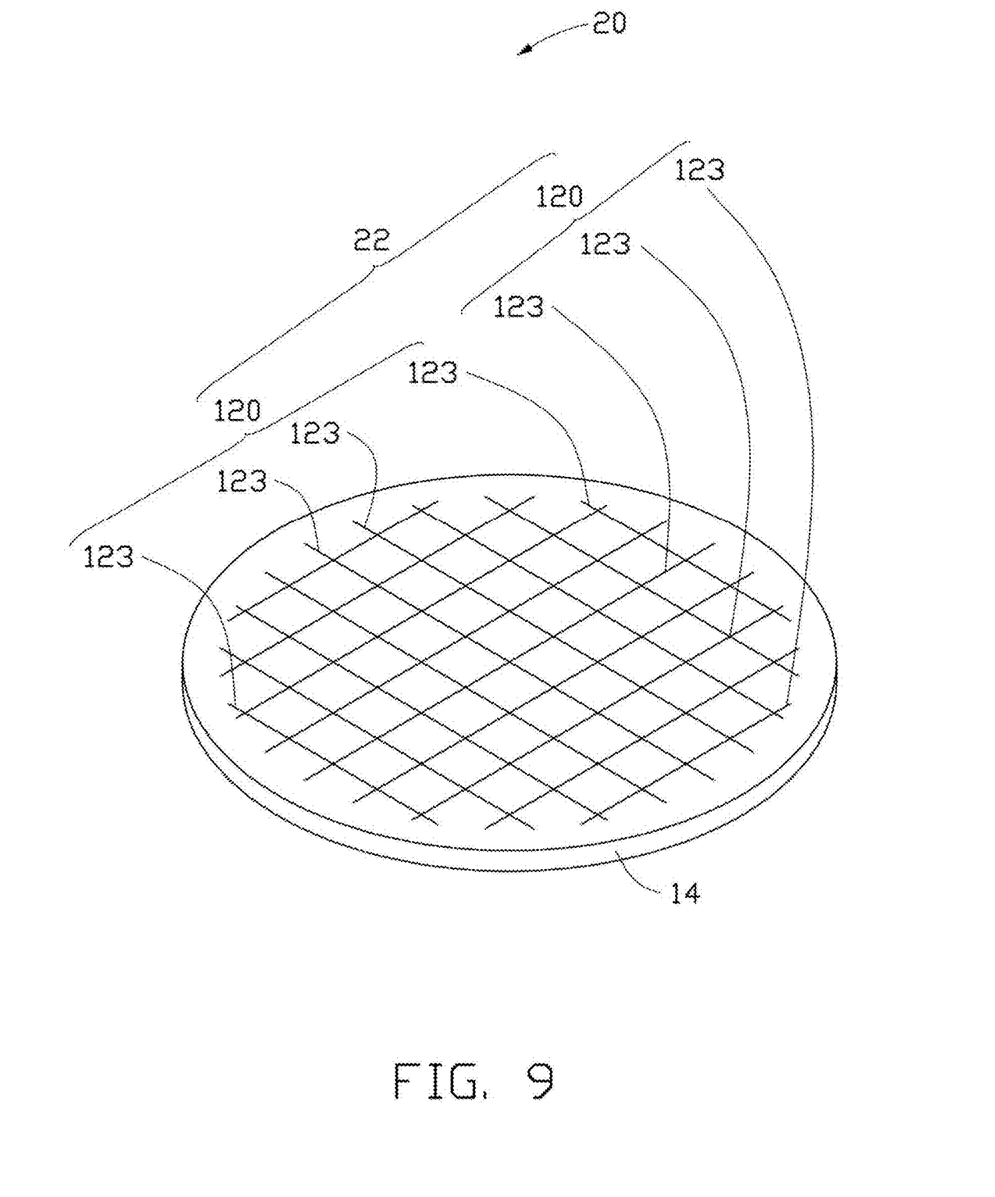
FIG. 9 is an isometric view of one embodiment of a culture medium.

Referring to FIG. 9, one embodiment of a culture medium 20 consists of a carbon nanotube structure 22 and the substrate 14 for loading the carbon nanotube structure 22. The carbon nanotube structure 22 includes two layers of carbon nanotube films. Each carbon nanotube film includes a number of carbon nanotube wires 123 extending substantially along a same direction. The carbon nanotube wires 123 in the two carbon nanotube films are substantially perpendicular to each other. As such a net structure is formed in the carbon nanotube structure 22. The distance of the adjacent carbon nanotube wires 123 in each carbon nanotube film are greater than or equal to 30 micrometers, and less than or equal to 80 micrometers. A diameter of each carbon nanotube wire 123 is larger than 1 micrometer, and less than or equal to 10 micrometers. The substrate 14 is a circular sheet-shaped plastic.

In one embodiment, a method for making the culture medium 20 includes: providing an original carbon nanotube structure consisting of two drawn carbon nanotube films, the carbon nanotubes in the two drawn carbon nanotube film define angles of about 90 degrees; fixing the original carbon nanotube structure on a frame and suspending the original carbon nanotube structure; spraying alcohol from a sprayer onto the original carbon nanotube structure to soak the original carbon nanotube structure, wherein during the spraying process, alcohol is atomized into several micrometer diameter drops and is taken out by a weak airflow and falling on the drawn carbon nanotube film; evaporating the soaked original carbon nanotube structure to converge the carbon nanotubes in each drawn carbon nanotube film into carbon nanotube wires 123, thereby forming the carbon nanotube structure 22; forming the carbon nanotube structure 22 into a circular shape, and placing it on a circular sheet-shaped plastic substrate 14; dropping alcohol on the circular carbon nanotube structure 22; and evaporating the alcohol to attach the circular carbon nanotube structure 22 to the circular sheet-shaped plastic substrate 14 tightly.

Figure 10:
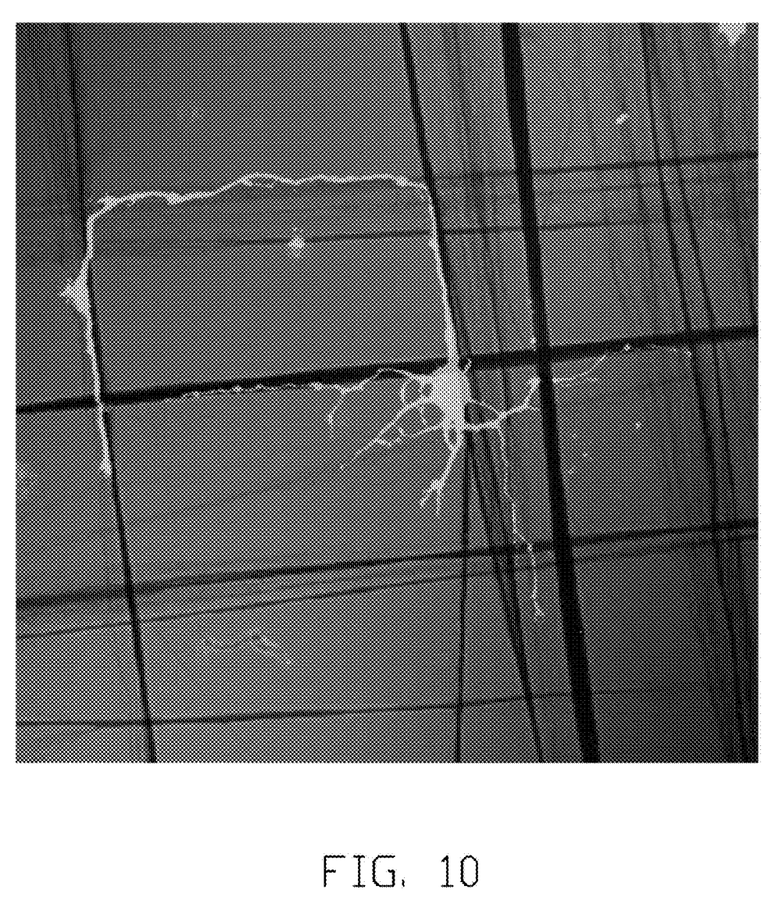
FIG. 10 is an optical microscopy image of one embodiment of neurons stained with fluorescence, wherein the neurons are cultured by using the culture medium shown in FIG. 9.

In one embodiment, a method for culturing neural cells using the culture medium 20 is similar to the method for culturing neural cells using the culture medium 10. Referring to FIG. 10, the carbon nanotube wires in the carbon nanotube structure 22 define a number of grids. The neurites extending from the neuron cells are absorbed on the grids of the carbon nanotube structure 22. The neurites substantially grow along the grids. The neurites can be formed into a folded linear structure guided by grids defined by the carbon nanotube wires.

Figure 11:
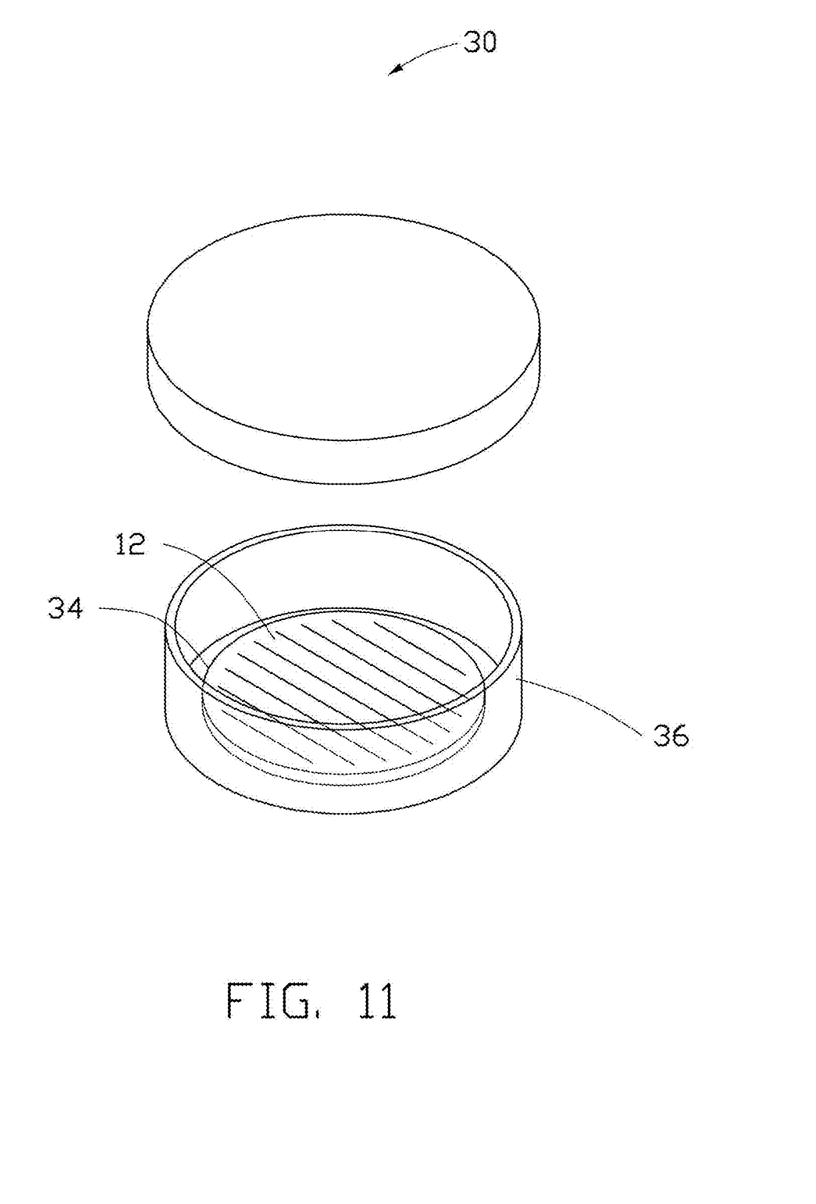
FIG. 11 is an isometric view of one embodiment of a culture medium.

Referring to FIG. 11, one embodiment of a culture medium 30 includes a substrate 34, a carbon nanotube structure 12 stacked on the substrate 34, and a container 36. The container 36 is used to load the substrate 34 and the carbon nanotube structure 12, and can receive liquid agents. The container 36 can be a culture vessel or a watch glass. The container 36 can be made of plastic, such as polystyrene. The substrate 34 can be a sheet-shaped structure. The substrate 34 is located between the carbon nanotube structure 12 and a bottom surface of the container 36. In one embodiment, the substrate 34 is a circular sheet-shaped polystyrene, the substrate 34 is fixed in the container 36 by an adhesive. The container 36 can grow neural cells using the culture medium 30. The culture medium 30 including the container 36 is convenient for storing and transporting.

In one embodiment, a method for making the culture medium 30 is similar to the method for making the culture medium 10. The method for making the culture medium 30 further includes step S340 after step S130 of the method for making the culture medium 10. The step S340 can fix the substrate with the carbon nanotube thereon in the container.

In one embodiment, the step S340 includes: providing a container 36 coated with an adhesive on the bottom of the container 36; placing the substrate 34 on the adhesive, with the substrate 34 located between the adhesive and the carbon nanotube structure 12; and heating the container 36 with the substrate 34 and the carbon nanotube structure 12 in a vacuum to remove toxic substances in the adhesive. During the heating process, the container 36, the substrate 34, and the carbon nanotube structure 12 will not deform or melt. A heating temperature can be less than or equal to 95 centigrade degrees. The heating time can be determined by the material of the container 36 and the substrate 34. In one embodiment, the heating temperature is larger than or equal to 80 centigrade degrees, and less than or equal to 95 centigrade degrees. The heating time is about 30 minutes.

In the step S340, the substrate 34 is tightly fixed in the container 36, and air bubbles between the carbon nanotube structure 12 and the substrate 34 can be removed by heating such that the carbon nanotube structure 12 can be tightly attached to the substrate 34.

A method for culturing neural cells using the culture medium 30 is substantially the same with the method for culturing neural cells using the culture medium 10.

Figure 12:
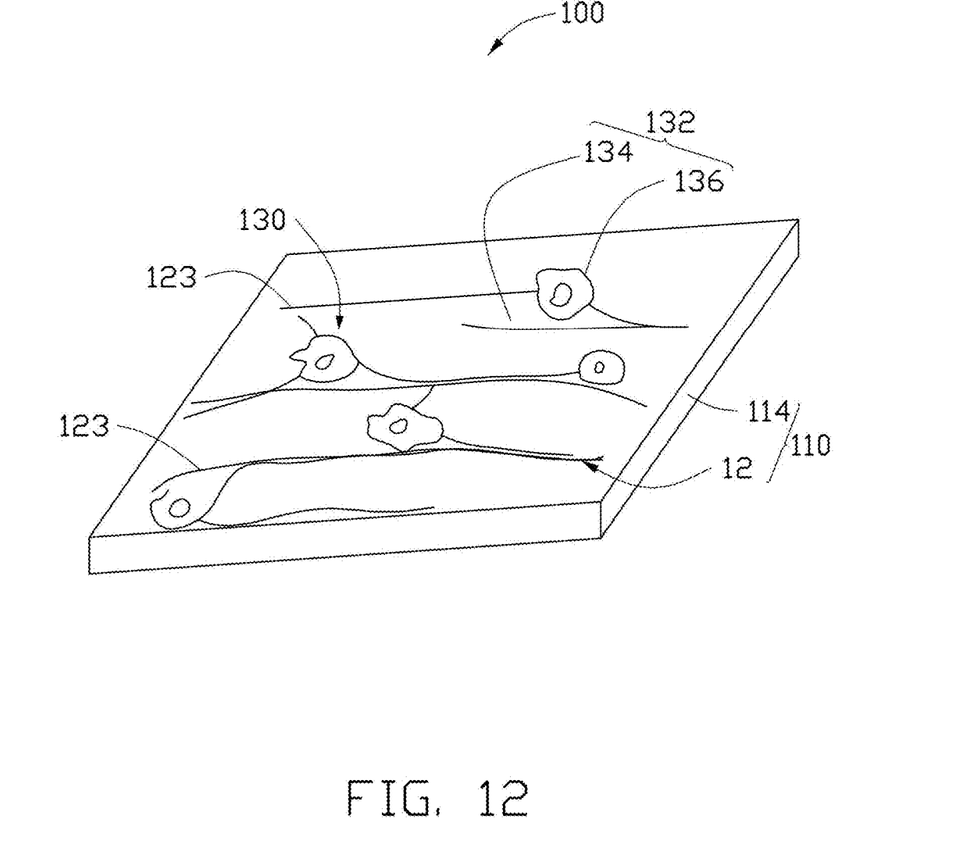
FIG. 12 is an isometric view of one embodiment of a neural graft using a culture medium.

Referring to FIG. 12, one embodiment of a nerve graft 100 includes a culture medium 110 and a neural network 130 absorbed on the culture medium 110. The culture medium 110 includes a biological substrate 114 and a carbon nanotube structure 12 located on the biological substrate 114. A surface of the carbon nanotube structure 12 is polarized to form the polar surface. The polar surface has a different surface charge from the neural network 130. Thus, the neural network 130 is absorbed on the culture medium 110. A material of the biological substrate 114 can be silicone, a biodegradable material, or biocompatible materials. The shape of the biological substrate 114 is not limited, and can be a sheet-shaped structure.

The carbon nanotube wires 123 are arranged in a certain order. The carbon nanotube wires 123 can be parallel to each other or crossed with each other forming a patterned structure. The neural network 130 includes a number of neural cells 132. The neural cells 132 are absorbed on the biological substrate 114. Each neural cell 132 includes a neural cell body 136 and at least one neurite 134 extending from the neural cell body 136. The neural cell body 136 is absorbed on the biological substrate 114. The at least one neurite 134 is substantially absorbed on the polar surface of the carbon nanotube structure, and substantially branches along the carbon nanotube wires 123. Each neurite 134 can be in a linear shape, folded linear shape, quadrangular shape, sector, or other curved shape. The shape of the neurite 134 can be controlled by the carbon nanotube wires 123 in the carbon nanotube structure 12. The at least one neurite 134 can be patterned. The arrangement of the carbon nanotube wires 123 in the carbon nanotube structure 12 can be determined by the shape of a wound. The extending direction of the neurite 134 can follow substantially along the carbon nanotube wires 123, and connect with edges of the wound part. The wound can then communicate with and connect to each other, thereby healing quickly.

In one embodiment, the nerve graft 100 includes a sheet-shaped silicone substrate, a single carbon nanotube film located on the silicone substrate, and a hippocampal neural network absorbed on the silicon substrate. The carbon nanotube wires in the carbon nanotube film extend substantially along a single direction and are juxtaposed. The hippocampal neural network includes a number of hippocampal neural cells. Each hippocampal neural cell branches a number of neurites. The neurites extend substantially along the carbon nanotube wires to form linear neurites.

It is to be understood that the above-described embodiments are intended to illustrate rather than limit the disclosure. Variations may be made to the embodiments without departing from the spirit of the disclosure as claimed. The above-described embodiments are intended to illustrate the scope of the disclosure and not restricted to the scope of the disclosure.

It is also to be understood that the above description and the claims drawn to a method may include some indication in reference to certain steps. However, the indication used is only to be viewed for identification purposes and not as a suggestion as to an order for the steps.

What is claimed is:

1. A method for making a culture medium for culturing neural cells, each neural cell comprising a neural cell body and neurite branched from the neural cell body, the method comprising:
   providing an original carbon nanotube structure comprising a drawn carbon nanotube film comprising a plurality of carbon nanotubes that are joined end to end by van der Waals force and are substantially oriented along the same direction;
   forming a carbon nanotube structure comprising a plurality of carbon nanotube wires spaced from each other by treating the original carbon nanotube structure, wherein a distance between adjacent two of the plurality of carbon nanotube wires is greater than or equal to a diameter of the neural cell body, the plurality of carbon nanotube wires are capable of guiding extending directions of the neurites; and the treating the original carbon nanotube structure comprises:
   forming a suspended original carbon nanotube structure;
   atomizing a solvent into a plurality of liquid drops, a diameter of each of the plurality of liquid drops is less than or equal to 10 micrometers;
   spraying the plurality of liquid drops into a surface of the suspended original carbon nanotube structure, using a flowing gas, to soak the suspended original carbon nanotube structure; and
   evaporating the plurality of liquid drops from the suspended original carbon nanotube structure to form the plurality of carbon nanotube wires, wherein a diameter of each of the plurality of carbon nanotube wires is greater than or equal to 1 micrometer and less than or equal to 10 micrometers, the distance between adjacent carbon nanotube wires is greater than or equal to 20 micrometers and less than or equal to 100 micrometers;
   fixing the carbon nanotube structure on a substrate; and
   forming a polar surface on the carbon nanotube structure using poly-D-lysine or polyetherimide.

2. The method of claim 1, wherein the original carbon nanotube structure comprises a plurality of drawn carbon nanotube films stacked with each other, and the plurality of carbon nanotubes in adjacent two of the plurality of drawn carbon nanotube films define an angle in a range from about 0 degrees to about 90 degrees.

3. The method of claim 1, comprising atomizing the solvent into the plurality of liquid drops is executed by gas atomization, ultrasonic atomization, or adding aerosol.

4. The method of claim 1, wherein the solvent is alcohol, methanol, acetone, acetic acid, or water.

5. The method of claim 1, wherein the step of forming the suspended original carbon nanotube structure comprises:
   providing at least one elastic supporter;
   suspending the original carbon nanotube structure by at least partly fixing the drawn carbon nanotube film on the at least one elastic supporter; and
   increasing a distance between juxtaposed carbon nanotubes of the plurality of carbon nanotubes by drawing the at least one elastic supporter along a direction substantially perpendicular to an extending direction of the plurality of carbon nanotubes.

6. The method of claim 5, wherein the elastic supporter is a spring, elastic rubber, or rubber ring.

7. The method of claim 1, wherein the step of fixing the carbon nanotube structure on the substrate comprises:
   putting the carbon nanotube structure on a surface of the substrate;
   soaking the carbon nanotube structure with an organic solvent; and
   evaporating the organic solvent from the carbon nanotube structure.

8. The method of claim 7, wherein the organic solvent is alcohol, methanol, acetone, or acetic acid.

9. The method of claim 1, further comprises placing the substrate with the carbon nanotube structure in a container, wherein the substrate is located between a surface of the container and the carbon nanotube structure.

10. The method of claim 9, wherein the placing the substrate with the carbon nanotube structure in the container comprises:
- applying an adhesive layer between the surface of the container and the substrate; and
- heating the container with the substrate and the carbon nanotube structure in a vacuum.

11. The method of claim 10, wherein the container is a culture vessel or a watch glass.

12. The method of claim 1, wherein a material of the substrate is selected from the group consisting of plastic, silicone, biodegradable material, and carbon nanotube.

13. The method of claim 1, wherein forming the polar surface on the carbon nanotube structure comprises:
- sterilizing the carbon nanotube structure; and
- treating the carbon nanotube structure by a poly-D-lysine solution or a polyetherimide solution.

14. The method of claim 13, wherein sterilizing the carbon nanotube structure comprises irradiating the carbon nanotube structure with ultraviolet light, or heating the carbon nanotube structure.

15. The method of claim 13, wherein the poly-D-lysine solution or the polyetherimide solution is dropped onto surface of the carbon nanotube structure, and the surface of the carbon nanotube structure is soaked by the poly-D-lysine solution or the polyetherimide solution for more than 10 hours.

* * * * *